(12) United States Patent
Yang et al.

(10) Patent No.: US 8,461,852 B2
(45) Date of Patent: Jun. 11, 2013

(54) METHODS AND APPARATUS RELATING TO FLUIDISED BEDS

(75) Inventors: Wuqiang Yang, Sale (GB); Haigang Wang, Manchester (GB)

(73) Assignee: The University of Manchester, Manchester (GB)

( * ) Notice: Subject to any disclaimer, the term of this patent is extended or adjusted under 35 U.S.C. 154(b) by 509 days.

(21) Appl. No.: 12/676,082

(22) PCT Filed: Aug. 22, 2008

(86) PCT No.: PCT/GB2008/002840
§ 371 (c)(1),
(2), (4) Date: Mar. 2, 2010

(87) PCT Pub. No.: WO2009/030876
PCT Pub. Date: Mar. 12, 2009

(65) Prior Publication Data
US 2010/0213953 A1    Aug. 26, 2010

(30) Foreign Application Priority Data
Sep. 3, 2007    (GB) .................................. 0717080.6

(51) Int. Cl.
*G01R 27/26*    (2006.01)

(52) U.S. Cl.
USPC .......................................... 324/664; 324/464

(58) Field of Classification Search
USPC .................................. 324/464, 664
See application file for complete search history.

(56) References Cited

U.S. PATENT DOCUMENTS
4,926,112 A    5/1990    Fasching
2007/0133746 A1    6/2007    Ortiz Aleman FOREIGN PATENT DOCUMENTS
EP    0157530 A2    12/1992
JP    2006136857 A    1/2006

OTHER PUBLICATIONS

Written Opinion of the International Searching Authority, issued Mar. 3, 2010, in related International Application No. PCT/GB2008/002840.
International Search Report, issued Mar. 12, 2009, in related International Application No. PCT/GB2008/002840.
International Preliminary Report on Patentability, issued Mar. 9, 2010, in related International Application No. PCT/GB2008/002840.
Chaplin, et al., "Application of electrical capacitance tomography to the fluidized bed drying of pahrmaceutical granule," Chemical Engineering Science, Oxford, GB, vol. 60, No. 24, Dec. 1, 2005, pp. 7022-7033.

(Continued)

*Primary Examiner* — Vincent Q Nguyen
(74) *Attorney, Agent, or Firm* — Jeffer Mangels Butler & Mitchell LLP

(57) ABSTRACT

A method and apparatus for producing particle density map images of fluidised particles by electrical capacitance tomography (ECT) in a fluidized bed apparatus allows for measuring online the liquid content of fluidized particles during the fluidization process and for recalibration of the fluidized particle permittivity during fluidization, allowing for online recalibration of an ECT system when the liquid content of particles changes, such as for fluidized bed drying or granulation processes. Recalibration measurements are made using reference electrodes positioned to measure the capacitance of the densely fluidized particles near the side walls of the fluidized bed. The electrodes of an ECT sensor array may be used to make the recalibration measurements which can be used to provide online liquid content measurement, such as moisture content, for the fluidized particles without stopping out stopping fluidization. The liquid content information may be used for process control. The method may also be used to provide separate images for solids distribution and for total liquid distribution across a plane being imaged.

17 Claims, 2 Drawing Sheets

OTHER PUBLICATIONS

Gareth Chaplin, et al., "The dynamic calibration of an electrical capacitance tomography sensor applied to the fluidized bed drying of pharmaceutical granule," Measurement Science and Technology, 10P, Bristol, GB, vol. 1, No. 6, Jun. 1, 2005, pp. 1281-1290.

Wuqiang Yang Ed, Anonymous, "Tomographic Imaging based on Capacitance Measurement and Industrial Applications," Imaging Systems and Techniques, 2007, IST '07, IEEE International Workshop On, IEEE, May 1, 2007, pp. 1-6.

Huang et al, "A High Frequency Stray-Immune Capacitance Transducer Based on the Charge Transfer Principle," IEEE Transactions on Instrumentation and Measurement, vol. 37, No. 3, Sep. 1988, pp. 368-373.

Yang et al, "New AC-based capacitance tomography system," IEEE Proc-Sci Meas. Technology, vol. 146, No. 1, Jan. 1999, pp. 47-53.

Search Report of the United Kingdom Intellectual Property Office, dated Feb. 6, 2008, in related UK Application No. GB0717080.6.

METHODS AND APPARATUS RELATING TO FLUIDISED BEDS

The present invention is concerned with capacitance measurement in fluidised beds containing particles, and a means for dealing with changes in particle permittivity, such as arising from changes in liquid content of particles, whilst carrying out electrical capacitance measurements and electrical capacitance tomography (ECT) imaging of the permittivity distribution of fluidised particles. The invention also relates to methods for the measurement of the liquid content, particularly the moisture content of fluidised particles.

In this description, the terms "fluidised bed" and "fluidised bed apparatus" refer to an apparatus comprising a base including a gas distributor plate, provided typically in the form of a mesh or a perforated plate, and side walls enclosing a fluidisation enclosure above the gas distributor plate. Typically, the gas distributor plate is held in a substantially horizontal plane during operation of the fluidised bed. A fluidisation gas is blown through the gas distributor plate in order to fluidise a bed of particles, which are present in the fluidisation space or enclosure. Typically, the particles are less than 4 mm in diameter, but often less than 1 mm in diameter. Such fluidised beds are well known for use in the drying or granulation of particles in the pharmaceutical, detergent and other industries. A minimum superficial gas velocity $U_{mf}$, measured as the mean gas velocity across the area of the gas distribution plate, is required in order to fluidise the particles. At higher velocities there will be a transition to a desired bubbling fluidised state.

For instance, granular particles containing a residual solvent, such as water, may be fluidised using heated gas, such as heated air, in order to remove the solvent from the particles. Fluidised beds may also be used for the agglomeration or granulation of fine particles into larger granules, for instance by the spraying of binder liquid droplets onto fluidised particles in a fluidised bed from a spray nozzle. Such processes are used in the pharmaceutical, agrochemical, detergent, coffee-making and other industries, for example, in the preparation of granular materials.

ECT has been used in order to monitor particle density distributions in fluidised beds by providing images of the permittivity distribution of fluidised particles across a plane through such a fluidised bed. Typically, this is achieved by mapping the measured permittivities for volume elements across a plane of measurement to corresponding pixels of a two-dimensional image, with the permittivities being shown, for instance, as different colours or represented by a contour map. An ECT sensor consists of a series or array of conductive electrodes placed around the periphery of the side walls of the apparatus, where fluidised particles are to be imaged. In order to obtain an image, usually, each electrode is sequentially supplied with an electrical potential while the others remain earthed or grounded. Hence, an electrical field is applied across a region to be measured in the measurement plane. To achieve an improved sensitivity and signal-to-noise ratio (SNR), more than one electrodes can be combined together and supplied with an electrical potential while the others remain earthed or grounded. From the interaction of this electric field with the material between the electrodes, the distribution of material phases (a high permittivity phase corresponding to the fluidised particles, and a low permittivity phase corresponding to the fluidisation gas) can be determined in the measurement plane contained (i.e. surrounded) by the array of electrodes. Note that the high permittivity changes with the liquid content of fluidised particles. For example, when the fluidised particles contain 30% water, typically the high permittivity value associated with the fluidised particles will be much higher than when they contain 2% water. Usually, the electric field for measurement of capacitance is applied by means of a high frequency voltage source, such as a signal generator, which provides a voltage and has a very low output impedance.

Although the ECT technique is of relatively low resolution, it is useful in the evaluation of rapid changes in hydrodynamic behaviour, such as the passage of individual bubbles through the fluidised particles when the fluidised bed is in a bubbling state. ECT images can be used to assist in the correct design and operation of fluidised beds. For industrial use in drying and granulation, the bubbling state is preferred for a fluidised bed.

ECT methodology has been described in detail in papers by Makkawi et. al., Chemical Engineering Science 57, 2411-2437, Tanfara et. al., Drying Technology 20, 1273-1289 and Sidorenko et. al., Powder Technology 141, 137-154 and hence will not be explained in detail here.

Previous studies applying ECT to fluidised beds generally use relatively dry powders, while the use of wet or liquid-containing particles was avoided due to the high relative permittivity of liquids, such as water, resulting in changes to the permittivity of the fluidised particles as liquid content changes during the operation of the fluidised bed (e.g. due to evaporation). The calibration of the ECT imaging apparatus relies on a knowledge of the permittivity values of both the high and low permittivity phases, and these are usually measured prior to operation of the fluidised bed, with the particles in a densely packed and unfluidised state for the high density (particles) phase permittivity. If this permittivity changes during operation of the fluidised bed, then the resulting images would be uncalibrated, and apparent density differences will be artefacts.

It is possible to obtain samples of particles from a fluidised bed, to measure their liquid content by an offline technique, such as oven drying, and then to correct the ECT signals by taking into account the change in the liquid content and its effect on the permittivity of the fluidised particles. This has a disadvantage that the correction is not instantaneously applicable, as it relies on an offline measurement of the liquid content, which may take several minutes.

It is also possible to recalibrate the ECT signals by stopping the fluidisation, such that the particles containing liquid form a packed bed, and then measuring the capacitance of the packed bed in order to obtain a new value for the high level permittivity to be used in the calculation of the tomographic image. This method was suggested by Chaplin et. al., Measurement Science and Technology, 16, 1281-1290. This has a disadvantage in practice that the method leads to discontinuous operation of a fluidised bed, which is usually not allowed in industry. Also, the wet particles in the bed may clump together once fluidisation has stopped.

In addition, without reliable online measurement of the liquid content in fluidised particles, it is not possible to implement optimum control of the fluidised bed.

Hence, it is desirable, for both monitoring and for process control purposes in relation to fluidised bed dryers and granulators, to be able to deal with changes in the permittivity of the fluidised particles (i.e. the high permittivity phase), as the liquid content in the fluidised particles changes during the operation of the fluidised bed. It is also desirable for this to be achieved by measuring the permittivity whilst the particles remain in a fluidised state. Also, because industrial processes are generally operated to produce particles of a specified liquid content, it is desirable to provide a direct, instantaneously available, measurement of the liquid content of fluidised particles in a fluidised bed apparatus, such as a dryer or a granulator, without the need to stop the fluidisation process. This could be conveniently used to monitor the end point of a process, such as drying or granulation, or could be conveniently used as a feedback parameter for process control of the fluidised bed. Similarly, ECT data could be used as a process control parameter, for instance leading to regulation of the fluidisation gas velocity or distribution in the event that the ECT image in the measurement plane shows undesirable behaviour. Until now, such feedback control of fluidised bed dryers, where the liquid content, and hence high level permittivity associated with the fluidised particles, is changing, have not been feasible.

It has now been found that it is possible to directly monitor the permittivity of the high permittivity phase for ECT measurement of fluidised particles in a fluidised bed apparatus by an instantaneous, online measurement technique, without the need to stop the fluidisation of the particles. It has also been found that it is possible to obtain an accurate measurement of the liquid content in the fluidised particles without the need to stop the fluidisation of the particles.

Measurements of capacitance form the basis of the image generated by an ECT sensor consisting of an array of sensing electrodes. For instance, for an 8 electrode ECT sensor array, there are 28 unique combinations of electrodes, resulting in 28 unique readings of capacitance measurements for each image. In order to implement the reconstruction technique to generate tomographic images, it is necessary to normalise the raw capacitance measurements ($C_M$). This normalisation is usually based on capacitance readings made in a packed bed of particles/solids or the dense phase filling the sensor ($C_H$) and with the fluidisation gas or the dilute phase, usually air, filling the sensor ($C_L$). These high and low capacitance measurements are typically performed prior to a fluidisation process and are applied to all 28 measurements. The normalised capacitance is defined as follows in equation I:

$$C_N = (C_M - C_L)/(C_H - C_L) \qquad \text{I}$$

The normalisation of the 28 measurements is valid as long as the permittivity of the two phases remains constant. The current invention is concerned with systems wherein the liquid content and hence the permittivity of the dense phase (i.e. the fluidised particles) changes whilst imaging is taking place. Since capacitance is almost proportional to permittivity and since liquids can often have a higher permittivity than the material of fluidised particles itself (for instance water has a relative permittivity of approximately 80 compared with a relative permittivity of approximately 2 to 4 for a dry pharmaceutical granule), the above calibration would not remain valid throughout a drying process using a fluidised bed apparatus, where the gas flowing through the fluidised bed is used to drive evaporation of liquid from the fluidised particles. Although the value of $C_L$ will remain fixed as it is determined by the permittivity of the fluidisation gas, typically air, the permittivity of the fluidised particles, i.e. the dense phase, will be influenced by the changes in the liquid content.

Surprisingly, it has been found that it is unnecessary to stop a fluidisation process in a fluidised bed in order to obtain the data needed to recalibrate the normalised capacitance. Even in a violently bubbling fluidised bed, the regions adjacent to the side walls of the bed, near the upper surface of the gas distribution plate, are found to be populated by a densely fluidised particle phase, which is almost free from bubbling. By positioning electrodes to measure the capacitance of these densely fluidised regions near the bottom of the fluidised bed, it is possible to obtain new values for $C_H$ to substitute into the equation for the normalised capacitance $C_N$. These values can be obtained, whilst the fluidised bed is still operating, allowing the tomographic imaging to instantaneously take into account any changes in the permittivity of the fluidised particles, and hence the fluidised bed is allowed to continue unhindered operation. Suitably, the electrodes of the ECT sensor array itself may be used to make the required measurements for the calibration purpose, typically by measuring capacitance between adjacent electrodes of the ECT sensor array, such that only the non-bubbling, densely fluidised particle material adjacent the side walls is accessed. Measurements of capacitance between the opposed electrodes could lead to undesirable artefacts because of the bubbles of gas leading to fluctuations in measured capacitance. For example, an 8-electrode ECT sensor can provide 8 capacitance measurements from adjacent electrode pairs. In most cases, the 8 capacitances are averaged and the averaged capacitance is used to derive the permittivity of the particles. If some of the 8 capacitance measurements is found significantly different from the averaged capacitance, say larger than 10%, it is suspected that the region between the two adjacent electrodes was not fully occupied by particles. In this case, this capacitance is excluded from the data set and the rest of capacitances are averaged again to obtain a new averaged capacitance.

Hence, in a first aspect, the invention provides a method for producing particle density map images of fluidised particles by ECT in a fluidised bed apparatus, the fluidised bed apparatus comprising a gas distributor plate and one or more side walls defining a fluidisation space, and an ECT sensor array positioned around the one or more side walls, wherein a first phase corresponding to fluidised particles having a first permittivity and a second phase corresponding to a fluidisation gas having a second permittivity are imaged, characterised in that the first permittivity used in calculating images is recalibrated during fluidisation of the particles to allow for changes in its permittivity value by using one or more recalibration capacitances measured by one or more pairs of reference electrodes positioned to measure the capacitance of densely fluidised particles near the one or more side walls.

Fluidised beds, to which the invention may be applied, can be of any shape, for instance, circular or rectangular bed shapes may be used. The term "side walls" is also used below when referring to a circular or conical fluidised bed, even though there may be only one continuous wall encircling the fluidised bed. The invention is applicable to both batch and to continuous fluidised bed drying processes. It is particularly applicable to processes, where the liquid content of the fluidised particles varies as the process proceeds, particularly fluidised bed drying of particles, such as pharmaceutical or detergent particles. Another suitable process, to which the invention is applicable, is fluidised bed granulation, where a liquid binder is sprayed onto fluidised particles. As the liquid content changes, the permittivity of the particles changes.

The gas distributor plate is a plate between the fluidised bed and the gas inlet of the fluidised bed apparatus, which allows the fluidisation gas to enter whilst preventing the particles being fluidised from falling down. It is suitably made in the form of a mesh or a perforated plate, where the holes in the mesh or plate are of smaller cross-section than the particles being fluidised.

The ECT sensor array comprises an array of electrodes, typically mounted in the same plane around the periphery of the fluidisation space of the fluidised bed, typically towards the bottom of the fluidised bed. The method of the invention also requires one or more pairs of reference electrodes positioned to measure the capacitance of particles on one or more side walls near the bottom of the fluidised bed. These pairs of electrodes may actually be electrodes of the ECT sensor array, or they may be separate reference electrodes. All the electrodes need to be electrically insulated from each other and from any extraneous conducting material. If the side walls of the fluidised bed are of a substantially non-electrically conducting material, such as glass or acrylic, then the electrodes may be positioned on the outside of the side walls. However, the electrodes could be placed within or on an inside surface of the walls. If the side walls are of an electrically conducting material such as metal, then the electrodes should be placed inside of the walls and electrically insulated from the walls.

The positioning of the electrodes to measure the capacitance of densely fluidised particles near the one or more side walls will depend upon the detailed design of the fluidised bed, to which the invention is applied. It has been discovered that in a bubbling fluidised bed, even in a violently bubbling fluidised bed, where the fluidisation velocity is 8 times, or even 10 times the minimum fluidisation velocity, or more, there are regions of densely fluidised particles, free from bubbling behaviour, near the side walls of the fluidised bed, particularly near the gas distribution plate, i.e. near the bottom of the fluidised bed. The meaning of "near" will depend upon the dimensions of the bed, but can be monitored and assessed for any particular fluidised bed process and apparatus, to which the invention is applied by means of ECT imaging. Typically, the densely fluidised region will be the region up to 20 cm, or up to 10 cm, or up to 5 cm above the gas distributor plate and within 5 cm, or within 2.5 cm, even within 1 cm of the side walls. Capacitances between all pairs of electrodes can be monitored online. From the data gathered, it is possible to select which pairs of electrodes should not be used if the material between them includes fluidising gas (e.g. air) bubbles.

In order to further increase the reliability of the capacitance measurements from the reference electrodes, it is preferred to measure the capacitances between a plurality of pairs of adjacent reference electrodes. Should any measured capacitance of the set of capacitance measurements be significantly different from the other measured values, for instance more than 10% different, or even more than 5% different then this measurement may be excluded from the calculation of the mean capacitance used to derive the moisture content of the fluidised particles. It may be assumed that such an anomalous measurement has arisen from the presence of a bubble of fluidisation air at the site of the measurements.

Hence, a plurality of recalibration capacitances are suitably measured between pairs of reference electrodes and a calculation of a mean recalibration capacitance, for recalibrating the first permittivity, is made from the plurality of recalibration capacitances. Suitably, when recalibration capacitances are measured between at least three pairs of reference electrodes, should a specific recalibration capacitance be substantially different from a mean of the other recalibration capacitances, the specific recalibration capacitance is excluded from the calculation of the mean recalibration capacitance.

Typically, the mean recalibration capacitance will be the arithmetic mean of the plurality of recalibration capacitances.

By measuring the permittivity of the densely fluidised particles in these regions, using electrode pairs specifically positioned to capture the capacitance of these regions, the first high permittivity, that is used for the particles in the calculation of images in the ECT method, can be recalibrated as the process progresses, and as imaging data are captured. For instance, the permittivity could be recalibrated after every 100 or 1000 images, or even between each imaging sequence if necessary, depending upon the computing power available, and the rapidity of change in the high permittivity of the fluidised particles. The second permittivity, corresponding to the fluidisation gas phase, does not need to be recalibrated and should remain relatively constant.

The superficial gas velocity used in the method of the invention is suitably from 1 to 10 times the minimum fluidisation velocity, preferably from 1 to 8 times, more preferably from 2 to 5 times. In many cases, a suitable fluidisation gas is air. Preferably, the method is applied to bubbling fluidised beds.

In order for the densely fluidised region of particles near the side walls to be accessed in the capacitance measurements, for each pair of reference electrodes, both reference electrodes are substantially on a same side of the fluidisation space. By this it is meant that the path across (i.e. joining the centres of) the electrodes should not substantially traverse the fluidisation space. Again, this will depend upon the detailed design of the fluidised bed used with the method of the invention. For a circular, cylindrical or conical bed, the angle subtended at the centre of the circle defining the walls should be suitably less than 60°, preferably less than 45°, more preferably less than 30°. For a rectangular bed, the same preferences apply, where the angle is subtended at the centre point of the rectangle. Suitably, for a rectangular bed, the reference electrodes are on the same side wall. Suitably, the centres of the reference electrodes are separated by a distance of 30 cm or less, preferably 20 cm or less. By centres of the reference electrodes is meant their centre of surface area, which is effectively the centre of mass of a two-dimensional shape having the same shape as the surface of the electrode.

Suitably the one or more pairs of reference electrodes are positioned near, preferably less than 20 cm from an upper face of the gas distributor plate, more preferably less than 10 cm. However, the most suitable position will depend upon the detailed design of the fluidised bed.

Suitably, each electrode of each pair of reference electrodes is at a distance from the upper face of the gas distributor plate, which is substantially the same for each reference electrode.

The reference electrodes may be substantially evenly spaced around the fluidisation space. It may be appropriate to measure the capacitances between several pairs of electrodes and to use individual capacitance measurements to determine the liquid content of the particles in the local regions or to use a mean value of the capacitance measurements to determine the mean liquid content of fluidised particles.

In particular, the reference electrodes may be the electrodes of the ECT sensor array. This is suitable when the ECT array is positioned at a suitable level of the fluidised bed where there are densely fluidised particles near the side wall of the fluidised bed. This allows for dual use of the ECT electrodes for both tomographic imaging and for recalibration of the sensor array.

The reference electrodes of each pair of reference electrodes are suitably adjacent reference electrodes in the ECT sensor array, meaning that no other measuring electrodes are situated between the pair of reference electrodes. Any suitable electrode arrangement may be used, for instance the electrodes may be positioned side-by-side on a side wall. Another suitable configuration would be a central circular electrode surrounded by an annular, concentric second electrode.

In one version of the invention the fluidised bed apparatus comprises two or more ECT sensor arrays positioned at different locations, i.e. at different distances from the upper face of the gas distributor plate, whereby images of the fluidised particles at different distances may be formed. The reference electrodes may be separate electrodes from those of the ECT sensor arrays, or may be electrodes of the lowest ECT sensor array.

The moisture content measurement can be influenced by the temperature of the particles, as the permittivity of liquid, particularly the permittivity of water, is a function of temperature. Preferably, the temperature of the fluidised particles is measured and the functional relationship between the moisture content of the fluidised particles and the measured capacitances takes into account the effect of the difference between the temperature of the fluidised particles and the reference temperature. The relationship between the permittivity of liquid and temperature can thus be factored into the functional relationship between the measured capacitance and the liquid content. A multi-order degree polynomial model may be used to compensate for the effect of temperature on the liquid measurement for each pair of electrodes.

A second aspect of the invention provides a method for measuring the liquid content of fluidised particles in a fluidised bed apparatus, the fluidised bed apparatus comprising a gas distributor plate and one or more side walls defining a fluidisation space, characterised in that calibration capacitances are measured during fluidisation by one or more pairs of reference electrodes positioned to measure the capacitance of densely fluidised particles near the one or more side walls, wherein the liquid content of the fluidised particles is derived from the calibration capacitance(s) by means of a functional relationship between the liquid content of the fluidised particles and the measured capacitance(s).

The functional relationship between the liquid content of the particles and the measured capacitance(s) is suitably derived by:
a) measuring capacitances between one or more pairs of reference electrodes when the particles, having a known liquid content, are fluidised at a reference temperature using a gas flow greater than or equal to a minimum fluidisation velocity for the particles,
b) repeating step (a) for a plurality of known liquid contents, and
c) establishing a functional relationship between the mean liquid content of the particles and the measured capacitances between the one or more pairs of reference electrodes for measuring the capacitance of densely fluidised regions of particles near the side walls of the fluidised bed.

For this second aspect of the invention, the preferred features and embodiments, detailed above for the first aspect of the invention, relating to the reference electrodes also apply to the second aspect of the invention. The reference electrodes for the second aspect of the invention are preferably positioned for measuring the capacitance of the regions of densely fluidised particles near the side walls of the fluidised bed. This means that bubbles passing through the fluidised bed do not lead to inaccuracies in the capacitance measurements from the reference electrodes. In order to further increase the reliability of the capacitance measurement by the reference electrodes, it is preferred to measure the capacitances between a plurality of pairs of adjacent reference electrodes. Should any measured capacitance of the set of capacitance measurements be significantly different from the other measured values, then this measurement may be excluded from the calculation of the mean capacitance used to derive the liquid content of the fluidised particles. It may be assumed that such an anomalous measurement has arisen from the presence of a bubble of fluidising gas at the site of the measurement.

The second aspect of the invention does not require the presence of an ECT sensor array, but suitably, the reference electrodes for the second aspect of the invention may be the electrodes of an ECT sensor array, which would be suitably positioned in order for its electrodes to act as reference electrodes, The liquid is suitably water, but other liquids or mixtures of liquids may be used with the method.

The liquid content measurement of the second aspect of the invention can be influenced by the temperature of the particles, as the permittivity of liquid, particularly the permittivity of water, is a function of temperature. Preferably, the temperature of the fluidised particles is measured and the functional relationship between the liquid content of the fluidised particles and the measured capacitance(s) takes into account the effect of the difference between the temperature of the fluidised particles and the reference temperature. The relationship between the permittivity of liquid and temperature can thus be factored into the functional relationship between measured capacitance and liquid content. A suitable capacitance model such as the Maxwell model may be used for taking into account the effect of temperature on the capacitance contribution from the liquid. Multi-order degree polynomials are used to compensate for the temperature effect on the liquid measurement for each pair of electrodes.

A third aspect of the invention provides a method according to a second aspect of the invention, wherein the liquid content of the fluidised particles is used as a feedback value for a process controller for controlling removal of liquid from the fluidised particles during fluidisation of the particles, wherein the process controller controls the temperature and/or flow rate of the fluidisation gas, which fluidises the particles. This aspect of the invention allows for control of fluidised bed drying processes, such as pharmaceutical granule drying, allowing for more efficient use of heated fluidisation gas and for reduced risk of damage to pharmaceutical components, which may be caused by overheating during the drying process. The conventional process control devices such as PI (proportional-integral) or PID (proportional—integral—differential) controllers may be used, combined with the liquid content information derived from the method of the invention, in order to follow a pre-determined drying curve.

This third aspect of the invention may also be applied to fluidised bed processes in which a liquid is added to fluidised particles, such as in fluidised bed granulation. Hence the invention provides a method according to the second aspect of the invention, wherein the liquid content of the fluidised particles is used as a feedback value for a process controller for controlling addition of liquid to the fluidised particles during the fluidisation process, wherein the process controller controls the addition rate of liquid and/or the temperature and/or the flow rate of a fluidisation gas, which fluidises the particles. In particular, the measured liquid content from the method of the invention may be used to indicate a granulation end point, minimising the risk of over-granulation and formation of clumps or agglomerates in the fluidised bed. Also, the superficial velocity and temperature of the fluidisation gas can be adjusted to suit the necessary fluidisation behaviour for particles with the measured liquid content. For instance, the particles with a high liquid content may need a greater superficial velocity of fluidisation gas.

A fourth aspect of the invention provides a fluidised bed apparatus for forming a bed of fluidised particles, the fluidised bed apparatus comprising a gas distributor plate and one or more side walls defining a fluidisation space, one or more pairs of reference electrodes positioned adjacent to the fluidisation space and adapted to measure the capacitance of densely fluidised particles near the one or more side walls and a means for calculating the liquid content of the fluidised particles, in a fluidised state, from one or more measured capacitance(s) between the one or more pairs of reference electrodes.

The means for calculating the liquid content of the densely fluidised particles, in a fluidised state, from the capacitance(s) of the densely fluidised particles measured between the one or more pairs of reference electrodes will typically be a computer running a computer program.

Typically, the method of the first aspect of the invention will generate an image which is a map of fluidised particle density in the plane being imaged, i.e. a particle density map image comprising a plurality of permittivity image pixels corresponding to each of a plurality of imaged volume elements in the fluidised bed apparatus, each image pixel showing or displaying an equivalent permittivity for each corresponding volume element. For example, pixels where the permittivity is within one certain specified range may be shown as having different colours from pixels where the permittivity is in a second, different specified range.

Because the particles can be treated as each having the same liquid content (measured on a weight/weight basis) at any particular time, and because the fluidising gas may be considered as having a uniform liquid (vapour) content (also on a weight/weight basis) at any particular time, the permittivity distribution effectively mirrors the particle distribution at any time, and this is the conventional manner for displaying ECT images. In other words, the image is conventionally shown as a map of permittivity across the plane being imaged, with the permittivity correlating with the fluidised particle density at any particular time, but also including the permittivity contribution of the fluidisation gas and the liquid in vapour form.

It is highly desirable, in a process where the liquid content of the fluidised particles is varying with time (and hence the liquid content of the fluidising gas will also be varying with time), to generate images or maps showing the actual fluidised solid particle distribution. Ideally, a further image can be generated showing a total liquid distribution (i.e. showing the liquid content for each imaged volume element, which is the sum of the liquid content contributed by the liquid in the fluidised particles and the liquid content contributed from liquid in vapour form in the fluidising gas for each volume element of the fluidising space—mapped to the corresponding pixel of the ECT image).

Hence the method of the first aspect of the invention may also be used to generate a solids distribution image comprising a plurality of solids distribution image pixels corresponding to each of the plurality of imaged volume elements in the fluidised bed apparatus, each solids distribution image pixel showing the solids content for each corresponding volume element.

Suitably, the method may also generate a liquid distribution image comprising a plurality of liquid distribution image pixels corresponding to each of the plurality of imaged volume elements in the fluidised bed apparatus, each moisture distribution image pixel showing the total liquid content for each corresponding volume element.

A preferred method for deriving such images is to treat the fluidisation gas as having a mean liquid content for the gas: $m_a$, throughout the fluidisation space at any specific time (expressed as the weight of liquid in vapour form per unit weight of fluidisation gas). Suitably, an inlet liquid content, and an outlet liquid content are measured for the fluidisation gas at any specific time whereby the mean liquid content of the fluidisation gas may be derived.

When the liquid is water, and an inlet temperature, an inlet relative humidity, an outlet temperature and an outlet relative humidity are measured for the fluidisation gas at any specific time, the average water content of the fluidisation gas may be derived using established relationships between the relative humidity of gases and their temperature. Similar methods may be used when the liquid is not water.

When the fluidisation process is a drying process, the fluidisation gas will have an outlet liquid content which is higher than the inlet fluidisation gas liquid content. For the sake of simplicity of calculation, the mean liquid content for the fluidisation gas may be taken to be the mean of the inlet and outlet liquid contents for the fluidisation gas.

Similarly, for the sake of simplicity, the fluidised particles may be treated as having a mean liquid content for the fluidised particles throughout the entire fluidisation space at any specific time (though in practice there may be small fluctuations around this mean).

With regard to the fluidisation gas temperature, this may also be derived from the measurements of inlet fluidisation gas temperature and outlet fluidisation gas temperature, or may be measured directly by temperature probes within the fluidised bed. These measurements may also be used to derive a mean temperature for the fluidised particles, which may be assumed to have the same mean temperature as the fluidisation gas within the fluidised bed.

A suitable method for deriving the mean liquid content for the fluidised particles is as for the second aspect of the invention, as detailed above. The preferred features of the second aspect are applicable here, where appropriate. The mean fluidised particle liquid content at any specific time may be derived from the recalibration capacitance(s) at that specific time by means of a functional relationship between the liquid content of the fluidised particles and the measured capacitance(s). This may be derived as detailed above for the second aspect of the invention. As explained above, it may also be necessary to measure the temperature of the fluidised particles to derive their liquid content, particularly when the permittivity of liquid is a function of temperature. In other words, the mean liquid content of the fluidised particles may be derived from the capacitance measured between the reference electrodes, using the known, previously determined relationship between the measured capacitance and the liquid content of the fluidised particles at any particular temperature.

The measured permittivity in any particular volume element $\epsilon$ is a function of $\epsilon_s$, the permittivity of the fluidised solids (derived from the capacitance measurement between the reference electrodes of the second aspect of the invention), the solids concentration in the volume element ($\phi$)) and the permittivity of the fluidisation gas $\epsilon_a$.

A simple model, such as Maxwell's equation, can be used to specify the relationship between $\epsilon_s$, $\epsilon_a$ and $\phi$:

$$\varepsilon = f(\phi, \varepsilon_s, \varepsilon_a) = \varepsilon_s \frac{2\varepsilon_s + \varepsilon_a - 2\phi(\varepsilon_s - \varepsilon_a)}{2\varepsilon_s + \varepsilon_a + \phi(\varepsilon_s - \varepsilon_a)}$$

Hence, if the permittivity of air $\epsilon_a$ is known, the solids concentration $\phi$ is derivable. However, the value of $\epsilon_a$ will depend upon the amount of liquid present as vapour in the fluidisation gas.

Now again using Maxwell's equation:

$$\varepsilon_a = f(m_a, \varepsilon_o, \varepsilon_w) = \varepsilon_w \frac{2\varepsilon_w + \varepsilon_o - 2m_a(\varepsilon_w - \varepsilon_o)}{2\varepsilon_w + \varepsilon_o + m_a(\varepsilon_w - \varepsilon_o)}$$

where $m_a$ is the liquid content of the gas, $\varepsilon_o$ the permittivity of dry gas and $\varepsilon_w$ the permittivity of the liquid. As mentioned above, the value of $m_a$ may be estimated from the measured liquid (vapour) content of the inlet fluidising gas and the outlet gas. For instance, it can be assumed to be the arithmetic mean of the inlet and outlet liquid contents.

Knowledge of $m_a$ allows $\varepsilon_a$, and hence $\phi$, to be derived for each volume element. This can be mapped to the corresponding pixel of the ECT image to give a solids distribution image.

Similarly, the liquid content of each volume element may be derived. The measured capacitance between the reference electrodes yields the permittivity of the fluidised solids $\varepsilon_s$ and from the known relationship between the liquid content of the fluidised solids and the solids permittivity, the liquid content of the fluidised solids $m_s$ may be derived.

$$\varepsilon_s = f(f_w, \varepsilon_{so}, \varepsilon_w) = \varepsilon_w \frac{2\varepsilon_w + \varepsilon_{so} - 2f_w(\varepsilon_w - \varepsilon_{so})}{2\varepsilon_w + \varepsilon_{so} + f_w(\varepsilon_w - \varepsilon_{so})}$$

Where $\varepsilon_{s0}$ is the permittivity of dry solids and $f_w$ is the proportion of liquid present in the solids. The value of $m_s$ will be $\phi \times f_w$.

A high frequency impedance analyser can be used to measure the capacitances between the pairs of electrodes. For instance, a suitable analyser is a Hewlett Packard HP4128. With regard to the frequency to be used in connection with the invention, measurements may be taken at any suitable frequency. Typically frequencies between 50 kHz and 13 MHz may be utilised.

Further aspects of the invention include the following, with preferred features of the previous aspects of the invention applying to these further aspects:

The use of capacitance measurements from an ECT sensor array of a fluidised bed apparatus to provide measurement of a liquid content for particles undergoing fluidisation by a fluidisation gas in the fluidised bed apparatus.

The use of capacitance measurements from an ECT sensor array of a fluidised bed apparatus to provide images of solid particle distributions in an imaged plane for particles undergoing fluidisation in the fluidised bed apparatus.

The use of capacitance measurements from an ECT sensor array of a fluidised bed apparatus to provide images of liquid distributions in an imaged plane for particles undergoing fluidisation by a fluidisation gas in the fluidised bed apparatus.

The invention will now be further described by means of example with reference to the accompanying drawings, in which.

Figure 1:
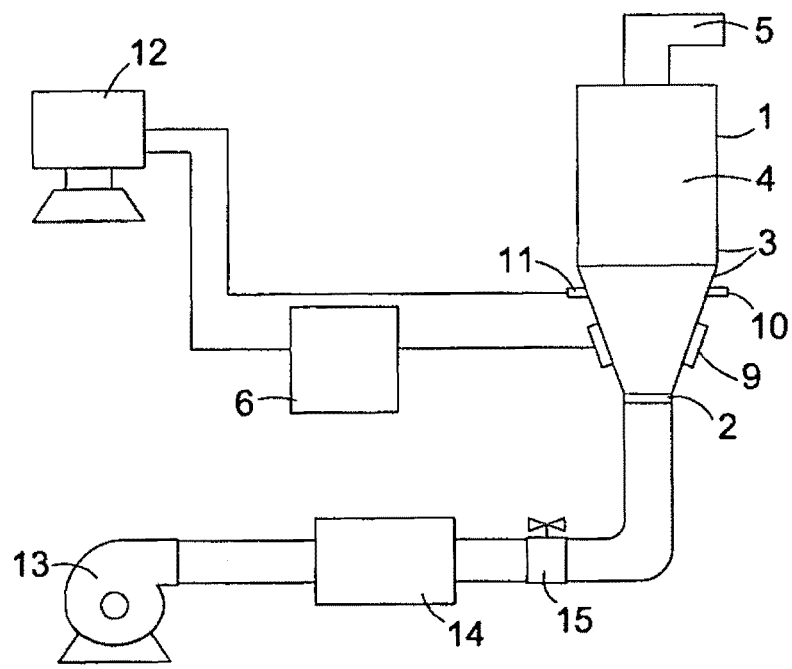
FIG. 1 shows a schematic diagram of a fluidised bed drying apparatus fitted with an ECT sensor array.

The fluidised bed dryer 1 comprises a gas distributor plate 2 and side walls 3 enclosing a fluidisation space 4. At the top of the dryer 1 is a gas outlet 5. An ECT sensor array 9 is mounted on the side wall 3. This conical side wall is made of glass in order to allow capacitance measurements to be made using ECT electrodes 7 mounded on the outside of the wall.

A control unit 6 controls the signals sent to the electrodes 7 of the ECT sensor array and measures the capacitances between the electrodes, sending a signal corresponding to these to the computer 12. Between each of the twelve electrodes 7 are mounted earthed contacts 8. The electrodes 7 and the earthed contacts 8 are held in a support 9 forming the ECT sensor array, and mounted in contact with the outside of the glass side wall 3. Note that electrical connections to the contacts and electrodes are not shown in FIG. 2. The support 9 is also provided with earth shielding to eliminate external interference.

A sample thief 10 is fitted to the side wall 3 to allow samples of fluidised particles to be taken from the fluidisation space 4. A thermocouple 11 mounted in the side wall 3 allows the temperature in the fluidisation space to be measured and the value sent to the computer 12.

The fluidisation gas, in this case air, is blown through the gas distributor plate 2 by means of a blower 13. The air passes through a heater 14 and a flow control valve 15. The gas distributor plate is a wire mesh having a 20 μm spacing.

The ECT system used is based on the AC capacitance measuring circuits with a data acquisition rate of 120 frames per second, as described in Yang and York (1999) IEE Proc-Sci. Meas. Technology 146 pages 47-53. However, this invention is not limited to the use of a particular ECT system. For example, the charge/discharge. ECT system designed by Songming Huang (1988) IEEE Trans. on Instrumentation and Measurement 37 (3) pages 368-373, or any other ECT system, may also be applicable.

The cylindrical part of the walls 3 is 16 cm in diameter with a height of 40 cm. The conical section is 10 cm in diameter at the bottom and 16 cm at the top, with a cone height of 10 cm. The air used for fluidisation is ambient air, with temperature in the range 15-85° C. achieved by use of the heater 14. The superficial air velocity is in the range 0.2-2.4 m/s. The superficial air velocity is defined as the average velocity across the inlet to the conical section at the gas distributor plate 2. For tests as model fluidised particles, semolina was used in the experiments detailed below, with an average particle diameter of 380 μm and a bulk density of 760 kg/m$^3$.

Wet semolina granules were prepared by spraying water onto the semolina whilst mixing in a low shear food mixer for 10 minutes. These were sieved to remove agglomerates greater than 1.5 mm in size, and about 2 kg of wet granular material was used in the fluidisation experiments. The granules were typical of Geldart B particles.

Figure 2:
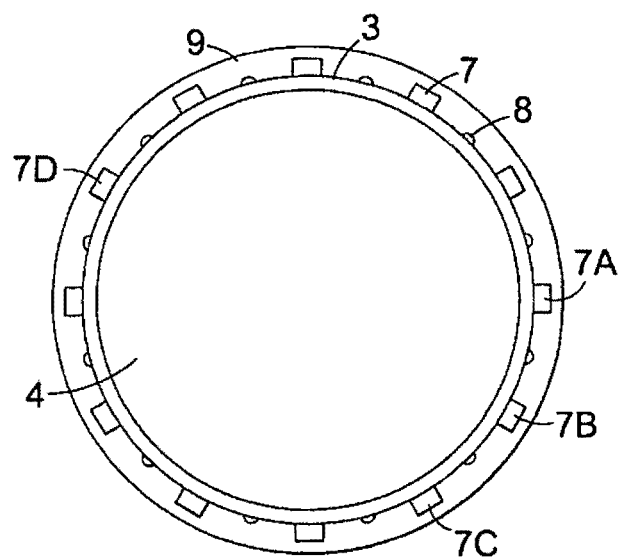
FIG. 2 shows a cross section though the plane of the ECT sensor array.

The capacitance measurements between neighbouring electrode pairs, such as 7A-7B in FIG. 2, at a constant moisture content, showed that the measured capacitance was essentially independent of the fluidisation gas velocity in the range from the minimum fluidisation velocity ($U_{mf}$) up to about 8 times the minimum fluidisation velocity. This was not the case for capacitances measured between opposite electrode pairs, such as 7B-7D in FIG. 2, where the capacitance falls with an increasing fluidisation velocity, presumably due to the bubbles of low permittivity phase passing between opposed electrodes.

Hence it was found that by measuring capacitance between adjacent electrodes, or between electrodes where the measurement path between the electrodes did not pass across the middle of the fluidised bed, the capacitance of a densely fluidised phase adjacent to the side walls of the fluidised bed apparatus could be measured, and that this measurement was independent of the fluidisation velocity over a wide range of operating conditions.

This then allowed for recalibration of the ECT imaging measurements, typically taken between adjacent electrodes. By measuring the changing capacitance between adjacent, or near adjacent electrodes as the permittivity of the particles changes due to the change in moisture, it was possible to use this measurement to recalibrate the ECT system as the experiment progressed, without any need to stop fluidisation in order to recalibrate the permittivity of the high permittivity phase (i.e. the wet particles). The permittivity derived from the capacitance measurements between adjacent or near adjacent electrodes of the ECT sensor array, while fluidisation continued, could be used to adjust the value of $C_H$ used in the normalised permittivity calculation (see equation I above).

It was also found that by measuring the moisture content of particles during a drying experiment, it was possible to obtain a functional relationship between the particle moisture content and the capacitance measured between adjacent or near adjacent electrodes of the ECT sensor array. This is because the permittivity of the wet granules is highly dependent upon their moisture content. In order to measure the moisture content of the granules during an experiment, 2.5 g of sample was taken using the sample thief 10 and a Mettler Toledo HB43 moisture meter used to measure the moisture content. From the functional relationship derived from these measurements, it was possible to then run a similar drying experiment and to predict the moisture content at any stage of the experiment from the capacitance measured between adjacent or near-adjacent electrodes, without needing to take samples or to stop fluidisation in order to measure the moisture content.

Figure 3:
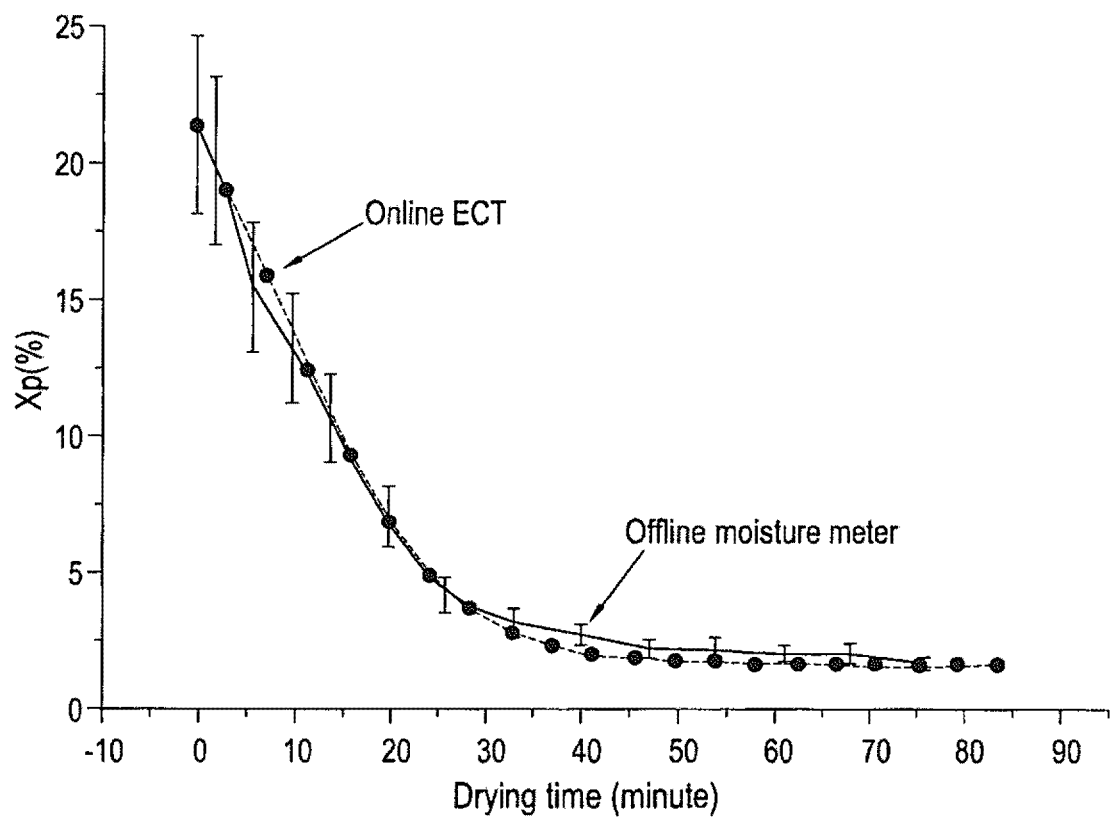
FIG. 3 shows a graph of solids moisture content (% by weight) versus drying time (minutes) for a fluidised bed of wet semolina granules as measured by offline sampling and as measured by the method of the second aspect of the invention.

FIG. 3 shows the results from such an experiment. In FIG. 3, the y axis shows the weight percent moisture content of the semolina granules (Xp%) as a function of drying time in minutes. The apparatus and particles used are as detailed above. The data points shown by error bars in FIG. 3 correspond to offline moisture measurements made on extracted samples measured with the moisture meter. The data points shown by filled circles correspond to the moisture value obtained from online capacitance measurement between adjacent pairs of electrodes in the ECT array and knowledge of the relationship between the measured capacitance, using the method of the second aspect of the invention, and the moisture content of the semolina granules. The correlation between the offline and the online values is excellent.

What is claimed is:

1. A method for producing particle density map images of fluidised particles by electrical capacitance tomography in a fluidised bed apparatus, the fluidised bed apparatus comprising a gas distributor plate and one or more side walls defining a fluidisation space, and an electrical capacitance tomography sensor array positioned around the one or more side walls, wherein a first phase corresponding to fluidised particles having a first permittivity and a second phase corresponding to a fluidisation gas having a second permittivity are imaged, characterised in that the first permittivity used in calculating images is recalibrated during fluidisation of the particles to allow for changes in its permittivity value by using one or more recalibration capacitances measured by one or more pairs of reference electrodes positioned to measure the capacitance of densely fluidised particles near the one or more side walls.

2. The method according to claim 1, wherein for each pair of reference electrodes, both reference electrodes are substantially on a same site of the fluidisation space.

3. The method according to claim 1 wherein the one or more pairs of reference electrodes are positioned near, preferably less than 20 cm from, an upper face of the gas distributor plate.

4. The method according to claim 1, wherein each reference electrode of each pair of reference electrodes is at a distance from the upper face of the gas distributor plate, which is substantially the same for each reference electrode.

5. The method according to claim 1, wherein the reference electrodes are substantially evenly spaced around, the fluidisation space.

6. The method according to claim 1 wherein the reference electrodes of each pair of reference electrodes are adjacent electrodes.

7. The method according to claim 1 wherein a plurality of recalibration capacitances are measured between pairs of reference electrodes and a calculation of a mean recalibration capacitance, for recalibrating the first permittivity, is made from the plurality of recalibration capacitances.

8. The method according to claim 7 wherein recalibration capacitances are measured between at least three pairs of reference electrodes and should a specific recalibration capacitance be substantially different from a mean of the other recalibration capacitances, the specific recalibration capacitance is excluded from the calculation of the mean recalibration capacitance.

9. The method according to claim 1, wherein the reference electrodes are the electrodes of the electrical capacitance tomography sensor array.

10. The method according to claim 9, wherein the fluidised bed apparatus comprises two or more electrical capacitance tomography sensor arrays positioned at different distances from the upper face of the gas distributor plate, whereby images of the fluidised particles at different distances from the upper face of the gas distributor plate may be formed.

11. The method according to claim 1 wherein the particle density map image is an image comprising a plurality of permittivity image pixels corresponding to each of a plurality of imaged volume elements in the fluidised bed apparatus, each permittivity image pixel showing a total permittivity for each corresponding volume element.

12. The method according to claim 11 wherein a solids distribution image comprising a plurality of solids distribution image pixels is generated corresponding to each of the plurality of imaged volume elements in the fluidised to apparatus, each solids distribution image pixel showing the solids content for each corresponding volume element.

13. The method according to claim 11 wherein a liquid distribution image comprising a plurality of liquid distribution image pixels is generated corresponding to each of the plurality of imaged volume elements in the fluidised bed apparatus, each moisture distribution image pixel showing the total liquid content for each corresponding volume element.

14. The method according to claim 11 wherein the fluidisation gas is treated as having a mean liquid content throughout the fluidisation space at any specific time.

15. The method according to claim 11 wherein an inlet liquid content, and an outlet liquid content are measured for the fluidisation gas at any specific time whereby the mean liquid content of the fluidisation gas is derived.

16. The method according to claim 11 wherein the fluidised particles are treated as having a mean liquid content for the fluidised particles throughout the fluidisation space at any specific time.

17. The method according to claim 16 wherein the mean liquid content for the fluidised particles is derived from the recalibration capacitance(s) at any specific time by means of a functional relationship between the liquid content of the fluidised particles and the measured capacitance(s).

* * * * *